United States Patent [19]

Winchell

[11] 4,364,920

[45] Dec. 21, 1982

[54] STABLE DIAGNOSTIC REAGENTS

[75] Inventor: Harry S. Winchell, Lafayette, Calif.

[73] Assignee: Medi-Physics, Inc., Emeryville, Calif.

[21] Appl. No.: 573,297

[22] Filed: Apr. 30, 1975

[51] Int. Cl.³ .................... A61K 49/00; A61K 43/00
[52] U.S. Cl. .......................................... 424/1; 424/9; 128/659
[58] Field of Search ....................... 424/1, 9; 128/659

[56] References Cited

U.S. PATENT DOCUMENTS

| | | | |
|---|---|---|---|
| 3,725,295 | 4/1973 | Eckelman et al. | 252/301.1 R |
| 3,735,001 | 5/1973 | McRae et al. | 424/1 |
| 3,740,418 | 6/1973 | Rajamani et al. | 424/1 |
| 3,787,565 | 1/1974 | Nouel et al. | 424/1 |
| 3,902,849 | 9/1975 | Barak et al. | 252/301.1 R |

Primary Examiner—Christine M. Nucker
Attorney, Agent, or Firm—Jon S. Saxe; George M. Gould; William H. Epstein

[57] ABSTRACT

Diagnostic reagents comprising a chelating agent and stannous tin which are suitable for conversion to radiopharmaceuticals by the addition of a radionuclide, such as suitable forms of technetium 99m, are stabilized against oxidation and/or hydrolysis by the addition to said complex of ascorbic acid, erythorbic acid, pharmaceutically acceptable inorganic salts thereof or mixtures thereof.

14 Claims, No Drawings

STABLE DIAGNOSTIC REAGENTS

BACKGROUND OF THE INVENTION

Diagnostic reagents which will reduce technetium from its commercially available valency state of plus seven to a lower valency state so that it may then be bound by a variety of chelating agents are recognized in the art. A large number of such reagents utilize stannous ions as the reducing agent for technetium. It is further recognized that it is necessary to maintain such reagents free of oxygen and oxidants since oxidation of the stannous ions and/or oxidation of the technetium will destroy the reduced technetium chelate.

Previous efforts to protect the reducing capability of stannous tin in such reagents prior to the addition of technetium 99 m pertechnetate include art-recognized means to remove oxygen and oxidants from the reagents and the use of lyophilization. Failure to effectively remove all oxidants, or the presence of residual water in the preparation after lyophilization, however, may result in the slow oxidation of the reducing agent and eventual failure of the reagent. An obvious expeditious solution to the problem would be to increase the concentration of the reducing agent thereby allowing for some loss in reducing power without losing the effectiveness of the reagents. This solution, however, is often undesirable wherein stannous ions are utilized as the reducing agent, since the potential for toxic manifestations increases as the concentration of the reagent administered to the patient is increased.

In addition to the problem of oxidation of the stannous ions in such reagents with resultant loss in stability, there is a second problem with such reagents which is not generally recognized in the art, i.e., alterations in the form of the reagent when the pH is elevated, thought to be due to the tendency of Sn(II) and reduced technetium in aqueous solution to hydrolyze with resultant alteration in the in vivo distribution pattern of the technetium 99 m labeled reagent.

In accordance with the present invention a means has been found to simultaneously stabilize such reagents against both problems enumerated above by the addition to said chelate of a non-toxic, physiologically acceptable, metabolizable substance selected from the group consisting of ascorbic acid, erythorbic acid, pharmaceutically acceptable inorganic salts thereof and mixtures thereof.

DETAILED DESCRIPTION OF THE INVENTION

The present invention pertains to a method of substantially increasing the stability of diagnostic reagents suitable for the preparation of radiopharmaceuticals by the addition of a radionuclide, said reagents comprising a chelating agent and stannous ions. Radionuclides to be added to the reagents stabilized in accordance with the invention are those which are in a high state of oxidation and which require reduction to allow chelation by the chelating agent. Such radionuclides include, for example, technetium 99 m as the pertechnetate, rhenium as the perrheniate, manganese as the permanganate and the like. The method comprises the addition to said chelates of a substance selected from the group consisting of ascorbic acid, erythorbic acid, pharmaceutically acceptable inorganic salts thereof or mixtures thereof. Polarographic evidence has established that by stabilizing said reagents in accordance with the method of invention a new tripartite coordination compound may be formed, i.e., ascorbic acid or erythorbic acid/Sn(II)/chelate. It is believed that one of the mechanisms of the reaction affecting stabilization in accordance with the present invention involves displacement of two of the waters of hydration on the coordination ring of Sn(II) or reduced technetium with electro-negative oxygens from ascorbic acid or erythorbic acid.

Samples of a Sn(II) chelate of ethane-1-hydroxy-1,1-diphosphonate (EHDP) prepared in accordance with McRae et al. U.S. Pat. No. 3,735,001, labeled with technetium 99 m and exposed to the atmosphere were found to substantially deteriorate in 24 hours. This deterioration was characterized by loss of Sn(II) reducing capacity and altered in vivo distribution of the technetium 99 m labeled reagent. Samples of the same reagent stabilized with ascorbic acid in accordance with the present invention were found to be stable in this regard for more than 48 hours after preparation. In addition to the above evidence, it has been demonstrated experimentally that stressing many of the Sn(II)/chelate diagnostic reagents by raising the pH will cause a substantial change in the in vivo distribution pattern of said reagent. For example, stressing the same bone-scanning Sn(II)/EHDP chelate by the addition of sufficient sodium hydroxide to raise the pH to 9.0 to 12.0 will significantly alter the in vivo distribution of the technetium 99 m labeled material. Stressing the same chelate stabilized by the addition of ascorbic acid in accordance with the present invention minimized the effect of elevated pH on the in vivo distribution of the technetium 99 m labeled material. It is therefore evident that stability has been achieved against both forms of instability described herein.

In accordance with the present invention, a chelate/Sn(II) diagnostic reagent which is suitable for the preparation of a radio-pharmaceutical by the addition of a radionuclide is treated with an amount of stabilizing substance selected from the group consisting of ascorbic acid, erythorbic acid, pharmaceutically acceptable inorganic salts thereof and mixtures thereof corresponding to from about 1 mole to about 100 moles of said stabilizing substance for each mole of stannous ion present in the reagent. More preferably, from about 3 moles to about 50 moles of said stabilizing substance are added for each mole of stannous ion present and, most preferably, said stabilizing substance is present in a molar ratio of about 10 moles for each mole of stannous ion. Regarding the upper molar limit given herein it should be noted that, although increases in the molar ratio of said stabilizing substance to stannous ion substantially in excess of 100:1 will increase the stability of the reagent, a point is reached wherein the stabilizing substance appears to compete with the chelating agent of the reagent for the technetium 99 m label when the reagent is labeled therewith. That such competition is taking place is evident by a significant increase in the amount of activity found in the kidneys, since it is known that ascorbic acid itself will form a coordination compound with technetium 99 m which will localize in the kidneys. This increase in uptake of activity by the kidneys, of course, detracts from the desired in vivo distribution wherein the reagent to be stabilized is intended for scintigraphic examinations elsewhere in the body, e.g., the bones. It is therefore readily apparent that care must be exercised in selecting the molar ratio of stabilizing substance to stannous ion since the resultant increase in stability may at the same time cause an alteration of the in vivo distribution pattern of the radiopharmaceutical. Furthermore, the proposed stabilizing materials are not efficacious for use with certain reagents used in radiopharmaceutical manufacture in which either all of the waters of hydration of the Sn(II) are displaced by the prosthetic groups of the chelate and/or in which the functional chelate is a relatively weak chelating agent for Sn(II) or reduced technetium and thus the stabilizing materials (e.g., ascorbic acid, erythorbic acid or salts thereof) may effectively compete with the primary functional chelate of the reagent. Examples of the former are thought to be Sn(II) pyrophosphate, and of the latter, Sn(II) glucoheptonate.

The diagnostic reagent chelates stabilized in accordance with the present invention are known in the art and are prepared by conventional methods. Generally such chelates are prepared by mixing the desired chelating agent with a soluble stannous salt, e.g., stannous chloride, in aqueous medium for a sufficient time to form the desired chelate. Depending on the chelating agent utilized, the pH of the solution will require adjustment to optimum levels and the reaction may be enhanced by agitation and/or gentle heating. Methods of preparing representative examples of such chelates are reported in the literature and the manipulative steps required are considered to be within the skill of the art. The method of incorporating the stabilizing substances of the present invention into the diagnostic reagents is not particularly critical to the invention and is also considered to be within the skill of the art. Since the reagents stabilized in accordance with the present invention are generally prepared in an aqueous medium, all that is required is the addition of ascorbic acid and/or erythorbic acid to said medium after the stannous ion-chelate is prepared and allowing sufficient time for equilibration to occur. Once the stabilized reagent is prepared in aqueous solution, it may be commercially packaged as such or subjected to lyophilization or other similar procedures known to the art.

In preparation of the stable reagents of the present invention it is important that appropriate measures be taken to minimize contact with oxygen. For example, containers therefor should be scrupulously cleaned and purged with nitrogen before filling to remove all traces of oxygen therefrom. The stable reagents of the present invention, whether packaged for commercial distribution in ampuls as a solution or in lyophilized form in suitable containers may also contain other ingredients recognized in the art such as preservatives against bacterial degradation, e.g., benzyl alcohol, the parabens and the like, buffers, particle-size stabilizers and the like.

The method of the present invention can be generally utilized to stabilize reagents of the type containing Sn(II) chelating agents which are suitable for the preparation of radiopharmaceuticals by the addition of radionuclides. Examples of such reagents include the Sn(II) chelates of: ethane-1-hydroxy-1,1-diphosphonate and polyphosphate, utilized in bone imaging; dimercaptosuccinic acid, utilized in kidney imaging; diethylaminetriamine pentaacetic acid, utilized in genitourinary tract and brain imaging; 2-mercaptoisobutyric acid, used in hepato-biliary imaging; and human serum albumin, utilized in blood pool imaging.

While ascorbic acid and erythorbic acid are preferred in the practice of the present invention, pharmaceutically acceptable inorganic salts thereof can be utilized. Preferred among such salts are alkali and alkaline earth salts, with the sodium and potassium salts being especially preferred. Further in accordance with the invention, while it is preferred to utilize ascorbic acid to form the stable diagnostic reagents described herein, it may be replaced in total or in any proportion with an equimolar amount of erythorbic acid.

The invention is further illustrated by the following Examples.

EXAMPLE 1

Aqueous reagent solutions having a 3 millimolar concentration of ethane-1-hydroxy-1,1-diphosphonic acid (EHDP) and a 1 millimolar concentration of stannous chloride with and without a 10 millimolar concentration of ascorbic acid were mixed with equal parts of normal saline solution containing 20 mCi/ml of technetium 99 m pertechnetate (no carrier added) and the mixtures were incubated in air at ambient temperature. After various times of incubation, 0.2 ml of each mixture was injected intravenously into rats and measurements were made of the percentage of activity remaining in the body 3 hours after administration which localized in the skeleton. The values obtained for the mixture not containing ascorbic acid after 10 minutes of incubation was $91.9 \pm 3.1\%$, and after 24 hours the value was $69.0 \pm 2.0\%$. The values obtained for the mixture containing ascorbic acid after 10 minutes, 24 hours, and 48 hours of incubation in air were $92.3 \pm 0.8\%$, $87.1 \pm 6.0\%$, and $90.5 \pm 1.6\%$, respectively. These data exemplify the ability of ascorbic acid to stabilize a Sn(II) EHDP reagent with regard to preservation of the localization of technetium 99 m reagent in bone following prolonged exposure to air.

EXAMPLE 2

Aqueous reagent solutions containing concentrations of 3 millimolar EHDP, 1 millimolar stannous chloride with and without either 10 millimolar ascorbic acid or 10 millimolar erythorbic acid were prepared. One part of each of the reagents was mixed with one part of normal saline solution containing 20 mCi/ml of technetium 99 m pertechnetate (no carrier added) and the mixture allowed to incubate in air for 72 hours at ambient temperature. At the end of 72 hours incubation, 0.2 ml of the mixture was administered intravenously to rats and the percentage of activity remaining in the body 3 hours after administration which localized in the skeleton was determined. The percentage in the control (no ascorbic or erythorbic acid added) was $55.9 \pm 6.3\%$, while with ascorbic acid added it was $80.1 \pm 4.3\%$, and with erythorbic acid added it was $87.3 \pm 2.6\%$. These results demonstrate the ability of erythorbic acid as well as ascorbic acid to provide temporal stability to the technetium 99 m labeled Sn(II) EHDP reagent.

EXAMPLE 3

Aqueous reagent solutions containing concentrations of 3 millimolar EHDP, 1 millimolar stannous chloride with and without 10 millimolar ascorbic acid were mixed with equal parts of saline solution containing 10 mCi/ml technetium 99 m pertechnetate (no carrier added). The pH of each mixture was increased to pH 9.0 and the mixture incubated for 15 minutes in air. 0.2 ml of the mixture then was administered intravenously to rats and the percentage of the activity remaining in the body 3 hours after administration was determined. For the control reagent not containing ascorbic acid, the percent of activity in the skeleton was $73.2 \pm 3.1\%$, while for the reagent containing ascorbic acid it was 89.0±2.1%. These results demonstrate the ability of ascorbic acid to provide stability with regard to elevated pH during short time intervals following such pH elevation.

EXAMPLE 4

A commercial lyophilized preparation of Sn(II) polyphosphate containing 100 mg sodium phosphate and 2 mg stannous chloride dihydrate was obtained. To one sample of this preparation, 50 micromoles of dry ascorbic acid was added. Five milliliters of normal saline solution containing 20 mCi/ml of technetium 99 m pertechnetate (no carrier added) was added to a sample of the preparation not containing ascorbic acid, and an identical aliquot of technetium 99 m pertechnetate in saline was added to the preparation to which ascorbic acid had been added. After 10 minutes, 24 hours, and 48 hours of incubation of each of the mixtures in air at ambient temperature, 0.2 ml of the mixture was administered intravenously to rats and the percentage of activity remaining in the body which accumulated in bone 3 hours after administration was measured. For the mixtures not containing ascorbic acid, the percentage of activity in bone after 10 minutes incubation was 67.2±6.2%. After 24 hours incubation the activity in bone was 17.3%, and at 48 hours the in vivo distribution of activity was that of free pertechnetate. For the mixtures containing ascorbic acid, the percentage of activity in bone after 10 minutes of incubation was 62.0±5.6%, after 24 hours incubation it was 58.6%, and after 48 hours incubation it was 57.3%. These data demonstrate the ability of ascorbic acid to temporally stabilize Sn(II) polyphosphate with regard to prolonged exposure to air.

EXAMPLE 5

Aqueous reagent solutions containing concentrations of 3 millimolar 2,3-dimercaptosuccinic acid (DMSA), 1 millimolar stannous chloride with and without 10 millimolar ascorbic acid were prepared. One part of each of the reagents was mixed with one part of normal saline solution containing 20 mCi/ml of technetium 99 m pertechnetate (no carrier added) and the mixtures allowed to incubate in air at ambient temperature for 20 minutes, 24 hours, and 48 hours prior to their intravenous administration to rats. One hour after administration, the rats were sacrificed and the concentration of activity in the kidneys expressed as percentage of activity retained in the body at that time (not excreted in the urine) was measured. For the mixture not containing ascorbic acid, the percentage of activity in the kidneys after 20 minutes, 24 hours, and 48 hours of incubation was 59.3±4.5%, 37.1±2.2%, and 32.5±4.0%, respectively. At corresponding times, the mixture containing ascorbic acid showed 60.5±3.4%, 58.7±1.8%, and 53.8±1.9% concentration of activity in the kidneys, respectively. These data demonstrate the ability of ascorbic acid to temporally stabilize Sn(II) DMSA with regard to prolonged exposure to air.

EXAMPLE 6

Aqueous reagents containing concentrations of 10 millimolar diethylenetriamine pentaacetic acid (DTPA), 1 millimolar stannous chloride with and without 10 millimolar ascorbic acid were prepared. One part of each reagent was mixed with one part of normal saline solution containing 20 mCi/ml of technetium 99 m pertechnetate (no carrier added), and the mixture was allowed to incubate in air at ambient temperature for 20 minutes, 21 hours and 48 hours. At the end of each incubation period, 0.2 ml of the mixture was administered intravenously to rats. One hour after administration the rats were sacrificed and the percentage of administered activity retained in the body was measured. The mixtures which did not contain ascorbic acid showed the following percentage of administered dose retained in the body at 1 hour after 20 minutes, 21 hours, and 48 hours of incubation: 12.3±2.9%, 89.9±1.0%, and 89.9±2.1%. The mixtures which contained ascorbic acid studied after the same time intervals of incubation showed 14.8±2.1%, 17.4±2.8%, and 15.9±2.7% retention, respectively. Preservation of the low retention of activity (i.e., high excretion) following incubation in air noted when ascorbic acid was added to the Sn(II) DTPA demonstrates the temporal stability achieved by addition of ascorbic acid to the reagent.

I claim:

1. A method of stabilizing a reagent suitable for the preparation of a radiopharmaceutical by the addition thereto of a radionuclide, said reagent comprised of a chelating agent and stannous ion comprising adding to said chelate from about 1 mole to about 100 moles of a substance selected from the group consisting of ascorbic acid, erythorbic acid, pharmaceutically acceptable inorganic salts thereof and mixtures thereof for each mole of stannous ion.

2. The method in accordance with claim 1 wherein from about 3 moles to about 50 moles of said stabilizing compound are added for each mole of stannous ion.

3. The method of claim 1 wherein about 10 moles of said stabilizing compound are added for each mole of stannous ion.

4. The method of claim 1 wherein said radionuclide is technetium 99 m pertechnetate.

5. The method of claim 1 wherein said stabilizing compound is ascorbic acid.

6. The method of claim 1 wherein said chelating agent is selected from the groups consisting of ethane-1-hydroxy-1,1-diphosphonate, polyphosphate, dimercaptosuccinic acid, diethylaminetriamine pentaacetic acid, 2-mercaptoisobutyric acid, and human serum albumin.

7. A stable reagent suitable for the preparation of a radiopharmaceutical by the addition thereto of a radionuclide which comprises a chelating agent, stannous ion and from about 1 mole to about 100 moles of a stabilizing compound selected from the group consisting of ascorbic acid, erythorbic acid, pharmaceutically acceptable inorganic salts thereof or mixtures thereof.

8. A reagent in accordance with claim 7 wherein said chelating agent is selected from the group consisting of ethane-1-hydroxy-1,1-diphosphonate, polyphosphate, dimercaptosuccinic acid, diethylaminetriamine pentaacetic acid, 2-mercaptoisobutyric acid, and human serum albumin.

9. A reagent in accordance with claim 7 wherein said chelating agent is ethane-1-hydroxy-1,1-diphosphonate and said substance is ascorbic acid.

10. A radiopharmaceutical comprising the stable reagent of claim 7 labeled with technetium 99 m.

11. A radiopharmaceutical comprising the stable reagent of claim 8 labeled with technetium 99 m.

12. A radiopharmaceutical comprising the stable reagent of claim 9 labeled with technetium 99 m.

13. A stable composition useful in the production of technetium-99 m based scanning agents comprising a stannous reducing agent, ethane-1-hydroxy-1,1-diphosphonic acid, and an effective amount of ascorbic acid sufficient to stabilize the composition.

14. A stable composition useful in the production of technetium-99m based scanning agents, comprising a stannous reducing agent, a chelating agent and an effective amount of ascorbic acid to stabilize the composition.

* * * * *